United States Patent
Reiffsteck

(10) Patent No.: US 6,655,220 B1
(45) Date of Patent: Dec. 2, 2003

(54) METHOD AND DEVICE FOR IN SITU TRIAXIAL TEST

(75) Inventor: Philippe Reiffsteck, Fontenay aux Roses (FR)

(73) Assignee: Laboratoire Central des Ponts et Chaussees, Paris (FR)

(*) Notice: Subject to any disclaimer, the term of this patent is extended or adjusted under 35 U.S.C. 154(b) by 0 days.

(21) Appl. No.: 10/110,817

(22) PCT Filed: Nov. 2, 2000

(86) PCT No.: PCT/FR00/03050
§ 371 (c)(1),
(2), (4) Date: Apr. 17, 2002

(87) PCT Pub. No.: WO01/33194
PCT Pub. Date: May 10, 2001

(30) Foreign Application Priority Data

Nov. 4, 1999 (FR) .............................. 99 13792

(51) Int. Cl.[7] ................................................. G01N 3/08
(52) U.S. Cl. ........................ 73/824; 73/152.59; 73/784; 73/818
(58) Field of Search .......................... 73/808, 818, 803, 73/821, 824, 825, 784, 152.48, 152.49, 152.59, 38

(56) References Cited

U.S. PATENT DOCUMENTS

4,649,737 A * 3/1987 Jones ............................. 73/38
5,435,187 A * 7/1995 Ewy et al. .................... 73/856

FOREIGN PATENT DOCUMENTS

FR 2 212 838 * 6/1972 ............. E02D/1/00

* cited by examiner

Primary Examiner—Edward Lefkowitz
Assistant Examiner—Jermaine Jenkins
(74) Attorney, Agent, or Firm—Cohen, Pontani, Lieberman & Pavane

(57) ABSTRACT

The device comprises a corer (1, 4) fitted with a flexible diaphragm (2) on its inside face, means (10) for driving the corer into the soil (11), means for breaking up the soil leaving the top orifice of the corer, means for applying axial forces on the diaphragm (2) and on the top face of the soil sample (12) contained in the corer, and means for measuring stresses and deformations to which the sample (12) is subject. While a measurement is being performed, the corer is held stationary in the soil (11).

5 Claims, 3 Drawing Sheets

METHOD AND DEVICE FOR IN SITU TRIAXIAL TEST

PRIORITY CLAIM

This is a U.S. national stage of application No. PCT/FR00/03050, filed on Nov. 2, 2000. Priority is claimed on that application and on the following application(s): Country: France, Application No.: 99 13792, Filed: Nov. 4, 1999.

The invention relates to a method for measuring the deformation moduluses of a soil sample in situ under conditions that are close to those of a triaxial compression test, and it also relates to apparatus for implementing the method.

Traditionally, direct measurement of the deformation moduluses of soil is performed by a "circularly-symmetrical triaxial compression test" method. For this purpose, a corer is used to take soil cores, and the use of a corer is not without incidence on the quality of the sample obtained. In spite of the sophistication of corers, it is found that reorganization occurs when the core penetrates into the casing because of the arching effect created by friction between the soil and the inside wall of the casing. The intermediate stages between taking the core and performing the test proper allow the initial stresses in the sample to relax. In order to test a sample that is remote from this suspected reorganized boundary region, the sample is generally cut down well away from the outside edges of the core. This precaution gives rise to a significant loss of material.

Laboratory testing, referred to as triaxial compression testing, is a homogeneous test that serves to identify the deformation moduluses of the soil that are required for deformation calculations, e.g. of the "finite element" type.

Triaxial compression testing consists in placing the test sample (which is generally cylindrical in shape having a section that is circular or square) in a cylindrical bag that is expandable. The bag is placed in an enclosure full of liquid whose pressure can be adjusted, and it is placed between two pistons which can exert forces on the end faces of the sample. Measurement devices serve to measure the displacements of the wall of the bag, the displacements of the pistons, and the pressures inside the enclosure and inside the soil. The deformation modulus is measured either by increasing the pressure inside the enclosure and the forces applied to the piston, in which case it is variation in the volume of the sample that is measured, or else by injecting a known volume of liquid into the enclosure and then measuring the resulting variation of pressure inside the sample.

U.S. Pat. Nos. 4,502,338 and 4,579,003 describe instruments for testing the samples under triaxial compression conditions.

Triaxial compression testing serves to measure the deformation moduluses directly. It also serves to monitor drainage conditions and to determine the anisotropy parameters of the soil under test.

Nevertheless it suffers from various defects. Firstly it is cumbersome to implement and consequently expensive since the idea is to study soil while it is still intact.

It also requires a great deal of time since it is necessary during the consolidation stage to recreate the initial stress field prior to performing the test. The result is also liable to be biased by various errors, due to slack in the contact surfaces and to errors of axial alignment in the mechanical stack constituted by the test machine.

In order to avoid some of those drawbacks, proposals have already been made to perform soil strength testing in situ, by means of tools that are expanded in a borehole.

FR 1 596 747 thus proposes a pressure-measuring boring sonde which comprises a sonde body provided on its outer perimeter with a flexible diaphragm and in which there is placed a hollow rod, and a cutting tool constituted by a sonde body and by a soil breakup member disposed in the hollow body and secured to the hollow rod.

That self-boring sonde can perform measurements as the borehole advances. However, the drawback of the measurements performed with that sonde is that the pressure-measuring test is based on the sonde expanding in a cylindrical cavity formed in soil of infinite dimensions. Unfortunately, under such conditions, the stress state generated in the soil is not homogeneous, and as a result deformation moduluses can be obtained only by applying empirical relationships which are difficult to develop.

Use of the pressure-measuring test has become a requirement when dimensioning foundations. Nevertheless, in the field of retaining earth and landslides, laboratory testing still remains essential.

The object of the invention is to provide a method and apparatus that make it possible, in situ, to establish a stress field that is uniform in a finite volume of soil under test, while avoiding any movement of the sample of soil for testing before the actual beginning of each test.

Another object is to propose a method and apparatus for in situ measurement of the moduluses of deformation of a soil sample under circularly-symmetrical triaxial compression testing conditions which can be used in particular in the field of retaining earth and landslides.

According to the invention, the method is characterized by the following steps:

driving a corer into the soil, the corer being fitted on its inside face with a flexible diaphragm;

removing the material that leaves the corer through its top orifice as it is being driven into the soil, so as to form a sample of soil for testing inside the corer;

holding the corer stationary in the soil in order to proceed with a measurement;

exerting pressure forces on the outside face of the diaphragm and on the top face of the sample so as to subject the sample to radial and axial stresses; and measuring the deformations to which the sample is subject.

Preferably, during measurement, the sample is subjected to predetermined radial stresses, and the axial stresses are varied until the sample breaks.

In order to determine the anisotropy parameters of the soil, a corer is used having an inside section that is substantially square.

The apparatus of the invention for implementing the method comprises:

a corer fitted on its inside face with a flexible diaphragm;

means for driving said corer into the soil in order to form a sample inside said corer;

means for removing the material which leaves said corer through its top orifice while the corer is being driven into the soil;

means for holding said corer stationary while taking a measurement;

means for applying an axial force to the top face of the sample;

means for applying pressure to the outside face of the flexible diaphragm;

means for measuring the radial and axial stresses to which the sample is subjected; and means for measuring the deformations to which the sample is subject.

Other advantages and characteristics of the invention appear on reading the following description made by way of example and with reference to the accompanying drawings, in which.

Figure 1:
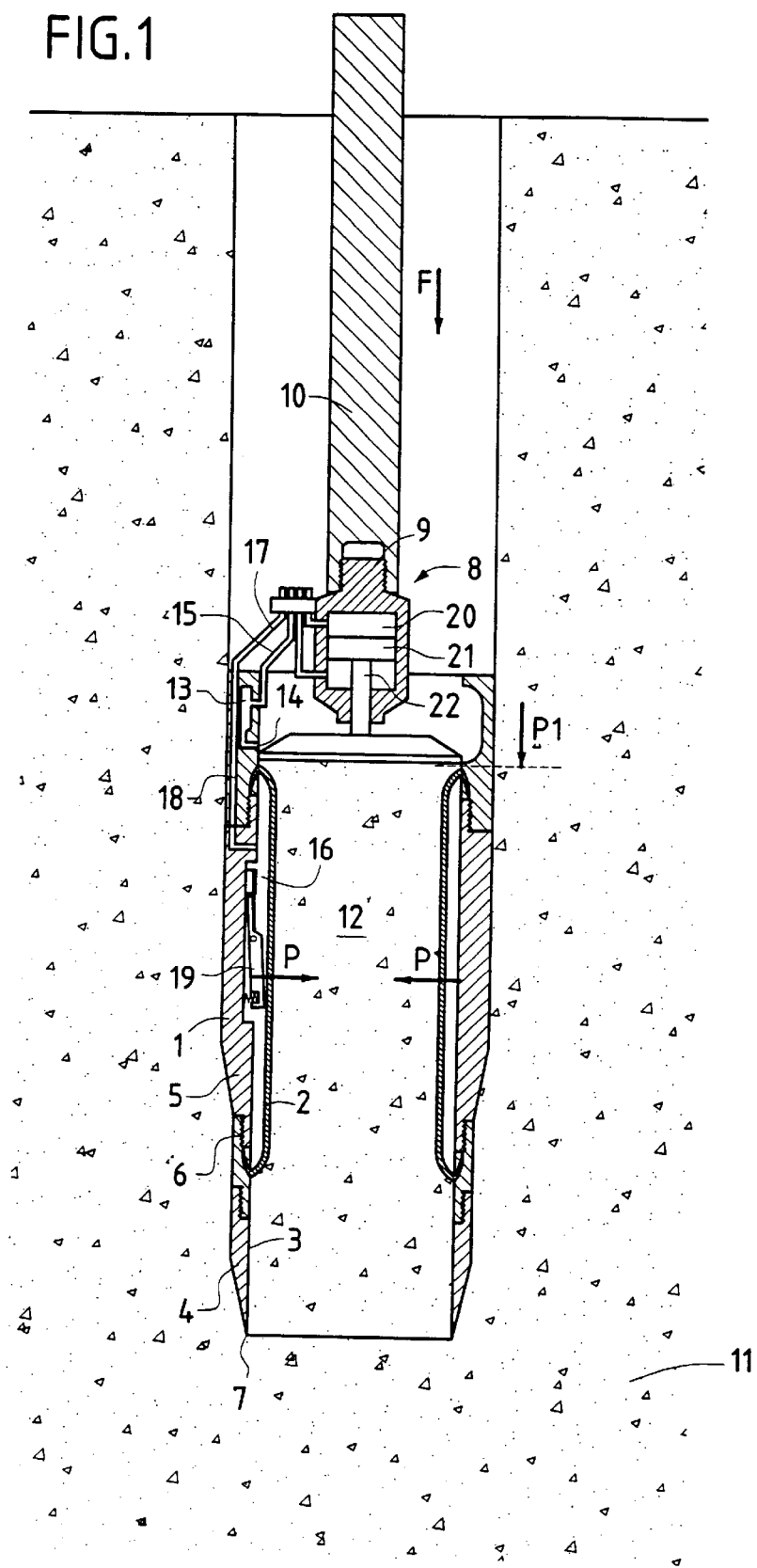
FIG. 1 is a section view on a vertical axial plane through apparatus of the invention while performing a measurement in situ.

The hollow body 1 of the sonde has a narrowing in its inside face serving as a housing for a flexible and expandable diaphragm 2 which, in the absence of any pressure forces on its outside face, lies in line with the inside wall 3 of a cutting shoe 4 fixed on the bottom end of a hollow body 1 by means of a screw thread 6. The cutting shoe 4 can thus be replaced in the event of its bottom end 7 of chamfered section becoming worn.

The top end of the hollow body 1 is connected to a tool head 8 which includes fixing means 9 on the bottom end of a jack rod 10 actuated by suitable means disposed on the surface of the soil under test.

When a vertical force F is exerted on the rod 10, the cutting shoe 4 penetrates into the soil 11 like a corer, and a sample 12 of soil penetrates into the cavity of the cutting shoe 4 and of the hollow body 1.

A passage 13 is formed in the inside wall of the hollow body 1, which passage opens out slightly above the top plane P1 of the diaphragm 2 via an orifice 14 having a jetting system mounted therein, which system is fed under high pressure by a slip of bentonite, for example, thus serving to break up the core of soil leaving the measuring zone. The passage 13 is connected to the surface via a duct 15 which delivers the slip.

The chamber 16 that exists between the diaphragm 2 and the inside face of the hollow body can be fed with fluid under pressure delivered from the surface via a duct 17 and a passage 18 formed in the hollow body 1. The chamber 16 also includes detector means 19 for detecting displacement of the diaphragm 2, and pressure measuring means, which means are connected to the surface by cables.

Figure 2:
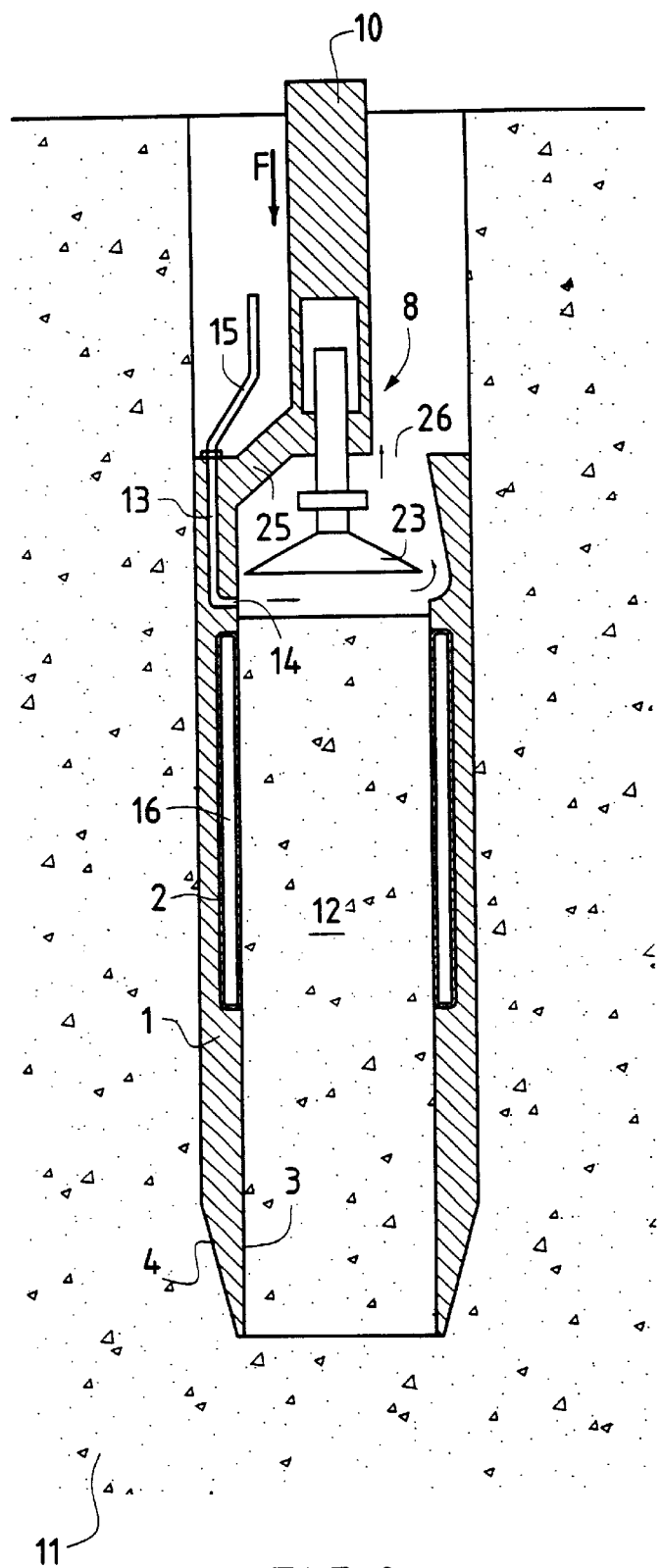
FIG. 2 is a diagrammatic section view through the FIG. 1 apparatus while it is being driven into the soil, showing the means for breaking up the soil on leaving the corer.
Figure 3:
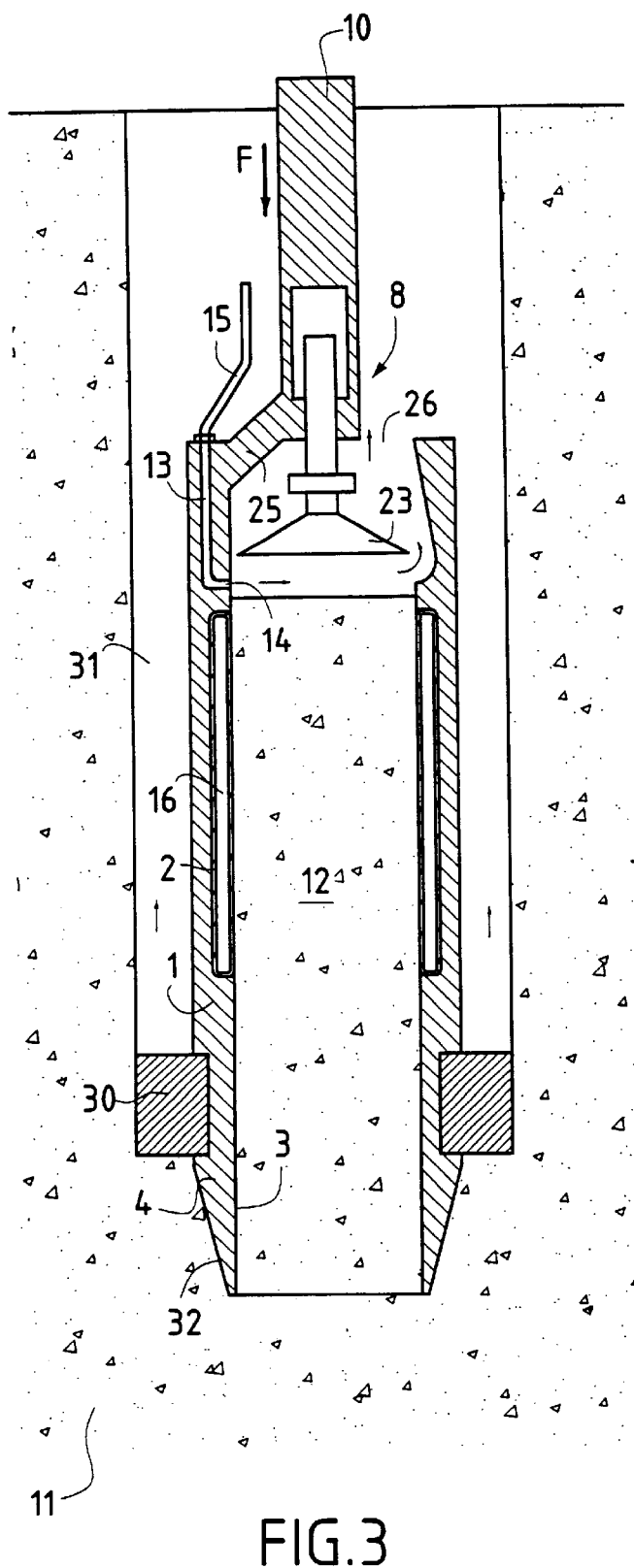
FIG. 3 is a diagrammatic section view through a variant embodiment of the apparatus.

The tool head 8 includes a cylindrical cavity 20 about a vertical axis having a double-acting drive piston 21 mounted therein with the piston rod 22 passing through the bottom face of the tool head 8. The bottom end of the piston rod is fitted with a second piston 23 whose diameter is substantially equal to the diameter of the hollow body 1. Vertical displacement of the drive piston 21 drives vertical displacement of the second piston 23. This second piston can take up a high position as shown in FIGS. 2 and 3 where it is situated above the plane of the orifice 14, which position is used while the sonde is being driven into the ground, and a low position as shown in FIG. 1 in which the bottom face is substantially level with the plane P1 and can exert a force on the top face of the sample 12 held captive in the diaphragm 2 and the cutting shoe 4. This low position is used during a measurement, and the force is generated by the drive piston 21. The two chambers of the cylindrical cavity 20, as separated by the drive piston 23 are connected to a hydraulic circuit which is controlled from the surface and which is not shown in the drawings.

The tool head 8 is connected to the hollow body 1 by arms 25 which leave between them passages 26 through which the mixture of slip and soil as broken up by the jetting system rises to the surface.

A measurement is taken as follows:

While the sonde is being driven into the soil, the chamber 16 is unpressurized, the second piston 23 is in its high position, and the jetting system is set into operation. The sonde is driven into the ground by the jack rod 10 through a depth that is not less than the height of the sonde. The sample 12 of the preceding measurement is broken up by the jetting system and a new sample 12 forms inside the diaphragm 2.

At the end of this driving operation, the jack rod 10 is held stationary, the jetting system is stopped, and the second piston 23 is pressed against the top face of the sample 12 with a small amount of force.

Thereafter the measurement proper is performed. To do this, the chamber 16 is put to a predetermined pressure P. The sample 12 is thus subjected to predetermined radial stress. Thereafter the axial stress applied to the sample 12 is varied by varying the force exerted on the top face of the sample 12 by means of the drive piston 21. During testing, the radial stress is kept constant and it is the axial stress which increases until the sample 12 breaks in shear.

By its very design, the proposed apparatus makes it possible to impose stress paths. This is done by servo-controlling the second piston 23 and the lateral pressure chamber 16. By making local measurements, it is possible to reach the range of small deformations. Local measurements are obtained by placing the sensors as close as possible to the sample 12, i.e. sensors of radial and axial displacements, together with an interstitial pressure sensor, all of which are fixed to the diaphragm 2.

In the embodiment described above, the hollow body 1, the cutting shoe 4, and the second piston 23 are circular in section.

The hollow body 1, the cutting shoe 4, and the second piston 23 could be of square section. Such apparatus makes it possible to implement a genuine triaxial compression test, and to determine the parameters of the anisotropy of the sample 12 under test.

FIG. 3 shows a variant embodiment of the cylindrical type in which the sonde body 1 has a breaking-up tool 30 on the outside and set back from the cutting shoe 4, which tool forms a well 31. This variant embodiment makes it possible to test materials of a variety of kinds that are difficult to take as samples, and also to test materials that are quite coarse.

The chamfered edge of the cutting shoe 4 is such that the inside face 3 of the bottom end of the shoe 4 is cylindrical, while the outside face 32 is conical and serves to push untested soil outwards away from the sonde while the sonde is being driven into the soil. The inside face 3 serves to smooth the sides of the sample 12 which have negligible influence on the measurements taken.

The apparatus of the invention can be used to perform a test that is similar to the circularly symmetrical triaxial compression test as performed in a laboratory. However efficiency is considerably improved because testing is performed step by step and almost continuously without large amounts of maneuvering.

What is claimed is:

1. A method of measuring in situ the deformation moduluses of a soil sample (12) under conditions close to those of a triaxial compression test, the method being characterized by the following steps:

driving a corer (1, 4) into the soil (11), the corer being fitted on its inside face with a flexible diaphragm (2);

removing the material that leaves the corer (1, 4) through its top orifice as it is being driven into the soil, so as to form a sample (12) of soil for testing inside the corer;

holding the corer (1, 4) stationary in the soil in order to proceed with a measurement;

exerting pressure forces on the outside face of the diaphragm (2) and on the top face of the sample (12) so as to subject the sample to radial and axial stresses; and measuring the deformations to which the sample (12) is subject.

2. A method according to claim 1, characterized by the fact that during measurement, the sample (12) is subjected to predetermined radial stresses, and the axial stresses are varied until the sample (12) breaks.

3. A method according to claim 1, characterized by the fact that a corer (1, 4) is used having an inside section that is substantially square.

4. Apparatus for measuring in situ the deformation moduluses of soil under the conditions of a triaxial compression test, the apparatus being characterized by the fact that it comprises:

a corer (1, 4) fitted on its inside face with a flexible diaphragm (2);

means (10) for driving said corer into the soil (11) in order to form a sample (12) inside said corer;

means for removing the material which leaves said corer through its top orifice while the corer is being driven into the soil (11);

means for holding said corer stationary while taking a measurement;

means for applying an axial force to the top face of the sample (12);

means for applying pressure to the outside face of the flexible diaphragm (2);

means for measuring the radial and axial stresses to which the sample (12) is subjected; and means for measuring the deformations to which the sample (12) is subject.

5. A method according to claim 2, characterized by the fact that a corer (1, 4) is used having an inside section that is substantially square.

* * * * *